US 6,551,617 B1

(12) United States Patent
Corbo et al.

(10) Patent No.: US 6,551,617 B1
(45) Date of Patent: Apr. 22, 2003

(54) TASTE MASKING COATING COMPOSITION

(75) Inventors: Michael Corbo, Flemington, NJ (US); Jatin Desai, Plainsboro, NJ (US); Mahesh Patell, Edison, NJ (US); Ronald Warrick, Sergeantsville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/553,513

(22) Filed: Apr. 20, 2000

(51) Int. Cl.$^7$ ................................. A61K 9/20
(52) U.S. Cl. ............. 424/465; 424/464; 424/489; 424/490; 424/497; 424/451; 424/452; 424/457; 424/458; 424/468; 424/469; 424/470
(58) Field of Search .................. 424/457, 458, 424/462, 463, 464, 465, 468, 470, 474, 480, 482, 484, 486, 489, 490, 497; 427/2.14

(56) References Cited

U.S. PATENT DOCUMENTS

| | | | |
|---|---|---|---|
| 3,453,360 A | 7/1969 | Hill | 424/22 |
| 3,520,970 A | 7/1970 | Lehmann et al. | 424/25 |
| 3,959,540 A | 5/1976 | Leiberich et al. | 428/35 |
| 4,101,651 A | 7/1978 | Kobayashi et al. | 424/35 |
| 4,321,117 A | 3/1982 | Kaetsu et al. | 204/159.16 |
| 4,321,253 A | 3/1982 | Beatty | 424/35 |
| 4,433,076 A | 2/1984 | Bauer et al. | 523/342 |
| 4,587,118 A | 5/1986 | Hsiao | 424/19 |
| 4,656,027 A | 4/1987 | Sjoovist | 424/495 |
| 4,710,384 A | 12/1987 | Rotman | 424/465 |
| 4,749,575 A | 6/1988 | Rotman | 424/441 |
| 4,760,093 A | 7/1988 | Blank et al. | 514/629 |
| 4,800,087 A | 1/1989 | Mehta | 424/497 |
| 4,839,177 A | 6/1989 | Colombo et al. | 424/482 |
| 4,851,226 A | 7/1989 | Julian et al. | 424/441 |
| 5,188,839 A | 2/1993 | Pearmain | 424/464 |
| 5,409,711 A | 4/1995 | Mapelli et al. | 424/490 |
| 5,472,708 A | 12/1995 | Chen | 424/451 |
| 5,489,436 A | 2/1996 | Hoy et al. | 424/441 |
| 5,552,152 A | 9/1996 | Shen | 424/441 |
| 5,639,475 A | 6/1997 | Bettman et al. | 424/466 |
| 5,654,004 A | 8/1997 | Okayama et al. | 424/479 |
| 5,707,646 A | 1/1998 | Yajima et al. | 424/439 |
| 5,817,340 A | * 10/1998 | Roche et al. | 424/470 |
| 6,004,582 A | * 12/1999 | Faour et al. | 424/473 |
| 2001/0007680 A1 | 7/2001 | Kolter et al. | 424/482 |

FOREIGN PATENT DOCUMENTS

| | | |
|---|---|---|
| EP | 0 352 800 A3 | 1/1990 |
| EP | 0 378 137 A3 | 7/1990 |
| EP | 0 523 847 B1 | 1/1993 |
| EP | 1110544 A2 | 6/2001 |
| FR | 2118999 A | 12/1971 |

* cited by examiner

Primary Examiner—Thurman K. Page
Assistant Examiner—Liliana Di Nola Baron
(74) Attorney, Agent, or Firm—Jonathan N. Provoost

(57) ABSTRACT

There is provided a coating composition that masks the undesirable taste of a pharmaceutically active ingredient, i.e. drug or medicine, that is consumed orally. The coating composition has polyvinyl acetate, and a dimethylaminoethyl methacrylate and neutral methacrylic acid ester. Optionally, an alkaline modifier may be included in the coating composition to enhance release of the active ingredient.

42 Claims, No Drawings

TASTE MASKING COATING COMPOSITION

BACKGROUND OF THE INVENTION

1. Field of the Invention

The present invention relates to a coating applied to the outside of a pharmaceutically active ingredient. More particularly, the present invention relates to a coating that masks the taste of a pharmaceutically active ingredient.

2. Description of the Prior Art

In general, there are two types of tablet dosage forms that are available in the marketplace, one that can be swallowed as a whole entity and the other as a chewable tablet. If the tablet is swallowed whole, the unpleasant taste of the pharmaceutically active ingredient is greatly minimized or avoided altogether. However, tablets formulated in a chewable form are designed for young children and for people with difficulty swallowing. Hence, the undesirable taste of the chewable tablet is mainly due to the bad taste of the pharmaceutically active ingredient. This can ultimately create a feeling of reluctance to taking medicine.

The use of a coating as part of a medicament is known. The coating is typically applied for the ease of swallowing and provides a barrier, which prevents the undesirable taste of the drug ingredient from coming through, making the drug preparation more palatable. In addition, this type of coating can be designed to act as a time release mechanism to control the rate of release of the medicine in the body. This can be accomplished in various ways such as adjusting the thickness of the coating and selection of the coating polymers/components that are used in these types of specialized coating formulations.

Various types of coatings can be applied to the outside of tablets and drug powders to achieve a specific desired effect. Enteric coatings are designed to be soluble in the intestine, where the pH is 6.5 or higher, but insoluble in the stomach, where the pH is lower. On the other hand, reverse enteric coatings are designed to be partially soluble in the stomach, i.e. under acidic or lower pH conditions, thereby releasing the drug in the stomach. Coatings can also be used for masking purposes including taste masking of chewable products.

Several U.S. patents are directed to taste masking. However, none disclose the coating of the present invention.

U.S. Pat. No. 4,851,226 issued on Jul. 25, 1989 to Julian et al. It provides a chewable medicament tablet made from granules coated with a blend of cellulose acetate or cellulose acetate butyrate and polyvinyl pyrrolidone.

U.S. Pat. No. 5,075,114, which issued on Dec. 24, 1991 to Roche, provides a taste masking and sustained release coating applied to a tablet. The coating blend is made with cellulose acetate and/or cellulose acetate butyrate and hydroxypropyl cellulose.

U.S. Pat. No. 5,489,436 issued on Feb. 6, 1996 to Hoy et al. This patent provides chewable tablets that have a coating consisting essentially of dimethylaminoethyl methacrylate and neutral methacrylic acid ester, and a polymer selected from the group consisting of cellulose acetate, cellulose triacetate, and mixtures thereof.

SUMMARY OF THE INVENTION

It is an object of the present invention to provide a coating or coating composition that coats a pharmaceutically active ingredient or particle and, thus, is part of a medicament.

It is another object of the present invention to provide such a coating that masks the undesirable taste, without delaying the availability of the pharmaceutically active ingredients when consumed orally.

It is also an object of the present invention to provide such a coating that is substantially insoluble in water and in a neutral pH environment, e.g. the mouth.

It is still another object of the present invention to provide such a coating that rapidly breaks down in an acid environment, such as in the stomach, thereby releasing the drug.

It is yet another object of the present invention to provide such a coating that readily dissolves, yet the rate of dissolution can be modified based on the composition.

It is a further object of the present invention to provide a medicament comprising a pharmaceutical active agent and the coating.

It is a still further object of the present invention to provide such a medicament in a variety of forms.

It is a still yet a further object of the present invention to provide a pharmaceutical composition comprising one or more pharmaceutical active agents coated with the coating of the present invention, which has an alkaline component in the coat composition that enhances the performance of the coat.

To accomplish the foregoing objects and advantages, the present invention, in brief summary, is a coating composition that masks the taste of a drug ingredient or medicine taken orally. The composition has (a) polyvinyl acetate, and (b) a dimethylaminoethyl methacrylate and neutral methacrylic acid ester.

In another embodiment, the coating composition of the present invention not only masks the taste of the medicine, but readily dissolves at an enhanced rate in an acid environment. The coating composition of this embodiment has (a) polyvinyl acetate, (b) a dimethylaminoethyl methacrylate and neutral methacrylic acid ester, and (c) an alkaline modifier.

DETAILED DESCRIPTION OF THE INVENTION

In the present application, a medicament is defined as a drug ingredient that is coated with a coating composition. Taste masking is defined as a perceived reduction of an undesirable taste that would otherwise be there.

The mouth is, for the most part, a neutral environment where the pH is about 7. One can mask the unpleasant taste of a drug by surrounding the drug ingredient, drug particle, or an agglomeration of drug particles with a coating composition that is insoluble in the mouth. The coating must be formulated to rapidly break down in the stomach to release the pharmaceutically active ingredient into the body. The present invention accomplishes this by providing a coating composition that effectively masks the unpleasant taste of a pharmaceutically active ingredient, i.e., drug or medicine, taken orally and immediately dissolves in an acidic pH environment, thereby releasing the pharmaceutically active ingredient in the stomach. Moreover, there is no noticeable after taste.

The coating composition of the present invention has a taste masking blend. The blend is (a) polyvinyl acetate, and (b) a dimethylaminoethyl methacrylate and neutral methacrylic acid ester. Additionally, the composition may include an alkaline modifier.

In a preferred embodiment, the present invention is a medicament having a drug ingredient, and a coating composition for masking the taste of the drug ingredient. The blend has (a) polyvinyl acetate and (b) a dimethylaminoethyl methacrylate and neutral methacrylic acid ester. Optionally, the coating composition of the medicament may have an alkaline modifier that enhances the release of the drug ingredient into one's body. That is, the inclusion of the alkaline modifier in the coating composition quickens the release of the drug ingredient in the stomach.

Polyvinyl acetate is the first component in the coating composition of the present invention. The polyvinyl acetate is insoluble in water. This property gives a composition containing polyvinyl acetate resistance to dissolution in the mouth. The polyvinyl acetate can be provided in its pure form or as a blend. BASF Corporation provides such a blend, commercially available under the tradename KOLLIDON SR. KOLLIDON SR is a blend that contains primarily polyvinyl acetate, polyvinylpyrrolidone, and minor amounts of sodium lauryl sulfate and colloidal silica.

The coating composition of the present invention includes about 3 percentage by weight or weight percent (wt. %) to about 97 wt. % of polyvinyl acetate of the total weight of the composition. Preferably, the polyvinyl acetate is included in an amount about 10 wt. % to about 70 wt. %, and more preferably, about 15 wt. % to about 50 wt. %. Above 50 wt. %, the polyvinyl acetate may be difficult to dissolve.

The dimethylaminoethyl methacrylate and neutral methacrylic acid ester is the second component in the present coating composition. This compound is available commercially from Rohm Pharma, and is sold under the tradename EUDRAGIT® E 100. EUDRAGIT® E 100 is supplied as colorless to yellow tinged granules with a characteristic amine-like odor. The structural formula is:

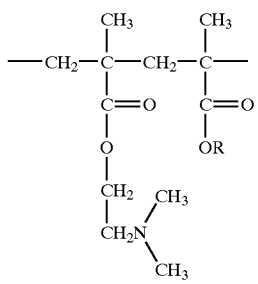

R = CH₃, C₄H₉

The dimethylaminoethyl methacrylate and neutral methacrylic acid ester is known to be soluble in acidic environments where the pH is up to about 5. At a pH greater than about 5, the ester is insoluble in water. Thus, the ester is relatively insoluble in the mouth where the pH is about 7.

The dimethylaminoethyl methacrylate and neutral methacrylic acid ester is in the present coating composition in an amount about 3 wt. % to about 97 wt. % of the total weight of the composition. Preferably, the dimethylaminoethyl methacrylate and neutral methacrylic acid ester is about 10 wt. % to about 40 wt. % of the total weight of the composition. The level of the dimethylaminoethyl methacrylate and neutral methacrylic acid ester that is included in the coating composition is determined by considering the cost of the raw material and the desired dissolution rate. For example, below about 10 wt. %, the dimethylaminoethyl methacrylate and neutral methacrylic acid ester does not dissolve as well as within the preferred range. Above 40 wt. %, the cost of this ingredient starts to become cost prohibitive.

The combination of the polyvinyl acetate and the dimethylaminoethyl methacrylate and neutral methacrylic acid ester has been found to mask the taste of the active ingredient.

In a preferred embodiment, an alkaline modifier may be included in the coating composition of the present invention. The alkaline modifier serves several functions. It acts as a stabilizer, buffering the microenvironment of the coating to a neutral pH, which enhances the coating integrity over coatings that do not contain an alkaline modifier. This improves the storage stability in a dry state or in a liquid suspension. The alkaline modifier, in a preferred embodiment, also functions as a plasticizer that reduces the brittleness of the coating. Moreover, it serves as a release modifier that increases the speed of dissolution of the coating in the acidic environment of the stomach. This function allows a medicament coated with the present invention to deliver the drug ingredient to the system more rapidly then other systems. This provides another improvement over coatings that do not have an alkaline modifier.

The alkaline modifier enhances the controlled rate of release or break down or dissolving in the acid environment of one's stomach. Thus, a preferred coating composition that has (a) polyvinyl acetate, (b) dimethylaminoethyl methacrylate and neutral methacrylic acid ester, and (c) the alkaline modifier, has both taste masking and enhanced release properties that increases the speed of dissolution of the coating in the acidic environment of the stomach. Accordingly, the drug ingredient is delivered more rapidly than by a coat that does not have an alkaline modifier.

Suitable alkaline modifiers are, for example, triethanolamine (TEA), basic amino acids, talc, ammonium oleate, meglumine, trimethylamine, calcium silicate, aluminum magnesium silicate, food alkalizing agents that are commonly used in the food industry, or mixtures thereof. The basic amino acids can be, for example, L-argenine, L-histadine, prolamine, or mixtures thereof. Moreover, zein (corn protein) or aluminum magnesium silicate may also be used in the present invention as an alkaline modifier.

An effective amount of the alkaline modifier may be added to the present coating composition. What is an effective amount varies according to the desired dissolution rate. The alkaline modifier is about 0.2 wt. % to about 20 wt. % of the coating composition. Preferably, the alkaline modifier is about 1 wt. % to about 15 wt. %, and more preferably, about 6 wt. % to about 12 wt. %.

In one preferred embodiment, the alkaline modifier is about 2 wt. % to about 4 wt. % triethanolamine, and about 4 wt. % to about 8 wt. % other alkaline modifiers.

In another embodiment, the present coating composition may also have additives incorporated into the coating composition. Such additives are, for example, polyvinylpyrrolidone (PVP), 2-vinyl pyridine (V)/styrene (S) copolymer, cellulose acetate, and mixtures thereof. PVP is a polymer, which is soluble in water. In water, PVP will dissolve and break down, permitting the release of the medicine in the stomach. The 2-vinyl pyridine (V)/styrene (S) copolymer preferably has a polymer weight ratio of V to S of about 65/35 or 80/20.

Ethyl cellulose may also be used as an additive in the coating composition. Preferably, the ethyl cellulose that is used, has a viscosity of about 5 to about 100 centipoise (cps) at 25° C., when made into a 2% solution. More preferably, the viscosity of the 2% solution of ethyl cellulose is about 30 to about 50 cps at 25° C. The ethyl cellulose is present in the coating composition in an amount about 10 wt. % to about 30 wt. %, preferably 20 wt. % to 30 wt. %.

The coating composition may also have one or more optional ingredients. Such optional ingredients are diluents, fillers, bulking agents, pigments, opacifiers, other plasticizers including PVP, processing aids, or mixtures thereof.

The present composition may also include typical processing aids. Such aids include, for example, sodium lauryl sulfate, colloidal silica, silicon dioxide, or mixtures thereof.

In a preferred embodiment, the coating composition of the present invention is about 28 wt. % polyvinyl acetate, about 28 wt. % dimethylaminoethyl methacrylate and neutral methacrylic acid ester, about 28 wt. % ethyl cellulose, about 5% talc, and about 3 wt. % to about 11 wt. % of other alkaline modifiers.

The ratio of the polymeric coating composition to pharmaceutical active ingredient is about 1:50 to 3:1. Preferably, the ratio is about 1:10 to 2:1. Most preferably, the ratio is 1:10 to 1.5:1. The pharmaceutically active ingredient is present in an amount, which typically is about 0.1 mg to about 1000 mg per unit dose.

The coated medicament can be, for example, chewable tablets, powders for reconstituted suspensions, regular liquid form of prepared suspensions, fast dissolving quick melt tablets, lozenges, wafers, chewing gums, hard shell gelatin capsules with powder/granules/liquid fills, soft shell gelatin with liquid center or filled with powder or granules, regular compressed tablets with immediate or delayed release, candy and candy bar forms, aerosol creams and gels.

There are many pharmaceutically active ingredients that can be coated with the taste masking system and/or the taste masking and controlled release systems of the present invention. For example, the systems can be applied to analgesics such as acetaminophen, aspirin, ibuprofen, dexibuprofen lysinate, naproxen, ketoprofen; antibiotics such as lactams, quinolones, macrolides and salts thereof; gastrointestinal drugs such as loperamide, famotidine, ranitidine, cimetidine and salts thereof; cardio vascular agents such as ibersartan, captopril, lisinopril and salts thereof; CNS drugs such as nefzodone, buspirone and salts thereof; antihistamines such as chlorpheniramine and astemizole; decongestants such as pseudoephedrine; cholesterol reducing agents such as statins; antivirals; anticancer; antiplatelet; vitamins; minerals; psyllium; or mixtures thereof.

A coated medicament may be prepared by using techniques and methods known in the art. For example, the coating composition of the present invention may be applied onto the drug active ingredient or medicine by using a fluidized bed coating operation.

To illustrate the present invention, the following examples are provided. However, it should be understood that the present invention is not limited to these examples.

In the examples, medicinal tablets were prepared as follows: (1) granules or crystals of a drug ingredient were coated with a coating composition in a fluid bed coater, (2) the coated granules or crystals were then combined with ingredients commonly used in making chewable/fast melting tablets and/or dry suspensions such as sugars, sweetners, and flavors, (3) the mixture was then compressed into tablet form to a hardness of about 10 Strong-Cobb units, using ¹¹⁄₁₆ inch round flat tooling. Each tablet had a weight of about 1550 mg.

Taste masking effectiveness is difficult to quantify. As set forth above, taste masking is understood to mean herein a perceived reduction of an undesirable taste that would otherwise be present. The examples demonstrate the taste masking benefits of the present invention, by measuring the percentage of a drug ingredient dissolved over a period of time under different pH conditions.

EXAMPLE 1

Coating (A) made of 27.78% KOLLIDONE SR, 27.78% Ethyl Cellulose, 28.0% Eudragit E® 100, 11.44% EASTMAN 9-45 (Acetylated Monoglyceride), and 5% Talc was applied to a drug ingredient, such as granules of acetominophen (APAP) or caffeine powder. The coated drug ingredient was then compressed into tablet form, forming medicinal tablets that were then subjected to dissolution testing in solutions having a pH of 7 and a pH of 1.2.

Tables 1 and 2 show the percentage of a drug ingredient dissolved over a given period of time in an environment where the pH is about 7, i.e. conditions similar to the mouth, and in an environment where the pH is about 1.2, i.e. conditions similar to the stomach.

TABLE 1

APAP with 30% Coating Add On of Coating A

| TIME (min) | Dissolution at pH = 7 | Dissolution at pH = 1.2 |
| --- | --- | --- |
| 0 | 0 | 0 |
| 1 | 4.9 | 4.9 |
| 6 | 22 | 45.6 |
| 11 | 32.4 | 61.9 |
| 16 | 42.1 | 71.5 |
| 21 | 51.2 | 77.8 |
| 26 | 59.8 | 81.6 |
| 31 | 67.3 | 85.3 |
| 36 | 73.8 | 87.8 |

TABLE 2

Caffeine with 30% Coating Add On of Coating A

| TIME (min) | Dissolution at pH = 7 | Dissolution at pH = 1.2 |
| --- | --- | --- |
| 0 | 0 | 0 |
| 1 | 2.1 | 6.1 |
| 6 | 22.7 | 77.5 |
| 11 | 37.2 | 90.6 |
| 16 | 52.2 | 92.3 |
| 21 | 65.2 | 92.7 |
| 26 | 74.7 | 92.2 |
| 31 | 81.1 | 93.2 |
| 36 | 85.5 | 93.5 |

The results indicate that dissolution is hindered by coating (A), in an environment where the pH is about 7, and dissolution is quicker in an environment where the pH is about 1.2. This demonstrates that the coating composition of the present invention inhibits the availability of the drug ingredient and thereby provides an effective means for masking the undesirable taste of a drug ingredient such as APAP or caffeine under neutral pH conditions, but provides rapid release of the drug ingredient in an acidic environment.

EXAMPLE 2

Coating (B) made of 27.78% KOLLIDONE SR, 27.78% Ethyl Cellulose, 28.0% Eudragit E® 100, 8.44% EASTMAN 9-45 (Acetylated Monoglyceride), 3.0% Triethanolamine, and 5% Talc was applied to a drug ingredient, such as granules of acetominophen (APAP) or caffeine powder. The coated drug ingredient was then compressed into tablet form, forming medicinal tablets that were then subjected to dissolution testing in solutions having a pH of 7 and a pH of 1.2.

Tables 3 and 4 show the percentage of a drug ingredient dissolved over a given period of time in an environment where the pH is about 7, i.e. conditions similar to the mouth, and in an environment where the pH is about 1.2, i.e. conditions similar to the stomach.

TABLE 3

APAP with 30% Coating Add On of Coating B

| TIME (min) | Dissolution at pH = 7 | Dissolution at pH = 1.2 |
|---|---|---|
| 0 | 0 | 0 |
| 1 | 1.5 | 4.5 |
| 6 | 11.8 | 56.3 |
| 11 | 17.5 | 81 |
| 16 | 21.8 | 91.8 |
| 21 | 28.8 | 96.4 |
| 26 | 35.1 | 98.1 |
| 31 | 41.6 | 98.9 |
| 36 | 47.9 | 99.3 |

TABLE 4

Caffeine with 30% Coating Add On of Coating B

| TIME (min) | Dissolution at pH = 7 | Dissolution at pH = 1.2 |
|---|---|---|
| 0 | 0 | 0 |
| 1 | 0.9 | 6.6 |
| 6 | 12 | 84.9 |
| 11 | 19 | 93.4 |
| 16 | 19.7 | 94.2 |
| 21 | 35.1 | 95 |
| 26 | 43.6 | 95.2 |
| 31 | 52.1 | 95.4 |
| 36 | 59.2 | 95.5 |

The results indicate that dissolution is hindered by coating (B), in an environment where the pH is about 7, and dissolution is quicker in an environment where the pH is about 1.2. This demonstrates that the coating composition of the present invention inhibits the availability of the drug ingredient and thereby provides an effective means for masking the undesirable taste of a drug ingredient such as APAP or caffeine under neutral pH conditions, but provides rapid release of the drug ingredient in an acidic environment.

EXAMPLE 3

Coating (C) made of 60.0% SENTRY BG-75 Pure PVA, 32.0% EUDRAGIT® E 100, 3.0% Triethanolamine, and 5% Talc was applied to a drug ingredient, such as granules of acetaminophen (APAP) or caffeine powder. The coated drug ingredient was then compressed into tablet form, forming medicinal tablets that were then subjected to dissolution testing in solutions having a pH of 7 and a pH of 1.2.

Tables 5 and 6 show the percentage of a drug ingredient dissolved over a given period of time in an environment where the pH is about 7, i.e. conditions similar to the mouth, and in an environment where the pH is about 1.2, i.e. conditions similar to the stomach.

TABLE 5

APAP with 30% Coating Add On of Coating C

| TIME (min) | Dissolution at pH = 7 | Dissolution at pH = 1.2 |
|---|---|---|
| 0 | 0 | 0 |
| 1 | 0.8 | 1.3 |
| 6 | 11.1 | 14.7 |
| 11 | 17.3 | 22 |
| 16 | 22.4 | 27.5 |
| 21 | 26.9 | 32.2 |
| 26 | 31 | 36.2 |
| 31 | 35 | 39.9 |
| 36 | 38.5 | 43.4 |

TABLE 6

Caffeine with 30% Coating Add On of Coating C

| TIME (min) | Dissolution at pH = 7 | Dissolution at pH = 1.2 |
|---|---|---|
| 0 | 0 | 0 |
| 1 | 1.1 | 3.1 |
| 6 | 13.6 | 24.7 |
| 11 | 23.3 | 36 |
| 16 | 31 | 43.8 |
| 21 | 37.8 | 49.8 |
| 26 | 43.4 | 55 |
| 31 | 49 | 59.7 |
| 36 | 52.9 | 64.1 |

The results indicate that dissolution is hindered by coating (B), in an environment where the pH is about 7, and dissolution is quicker in an environment where the pH is about 1.2. This demonstrates that the coating composition of the present invention inhibits the availability of the drug ingredient and thereby provides an effective means for masking the undesirable taste of a drug ingredient such as APAP or caffeine under neutral pH conditions, but provides rapid release of the drug ingredient in an acidic environment.

Having thus described the present invention with particular reference to preferred embodiments thereof, it will be apparent that various changes and modifications may be made therein without departing from the spirit and scope of the present invention as defined in the appended claims.

What is claimed is:

1. A coating composition for masking the taste of a drug ingredient or medicine and for providing rapid and substantially complete release of the drug ingredient or medicine in the stomach when the drug ingredient or medicine is coated with the composition, comprising a taste masking blend of:
   (a) polyvinyl acetate;
   (b) dimethylaminoethyl methacrylate and neutral methacrylic acid ester; and
   (c) an alkaline modifier; the alkaline modifier being present in the coating composition, as a component thereof, in an amount sufficient to increase the coating composition's dissolution rate in the stomach as compared to a like composition that does not contain the alkaline modifier, said drug ingredient or medicine, when coated with the coating composition and orally ingested, having its taste masked in the mouth then being rapidly and substantially completely released in the stomach.

2. The composition of claim 1, wherein said polyvinyl acetate is about 3 wt. % to about 97 wt. % of the total weight of the composition.

3. The composition of claim 1, wherein said dimethylaminoethyl methacrylate and neutral methacrylic acid ester is about 3 wt. % to about 97 wt. % of the total weight of the composition.

4. The composition of claim 1, wherein said alkaline modifier is selected from the group consisting of triethanolamine, basic amino acids, talc, ammonium oleate, meglumine, trimethylamine, calcium silicate, aluminum magnesium silicate, food alkalizing agents, and mixtures thereof.

5. The composition of claim 4, wherein said alkaline modifier is triethanolamine.

6. The composition of claim 1, wherein said alkaline modifier is about 0.2 wt. % to about 20 wt. % of the total weight of the composition.

7. The composition of claim 6, wherein said alkaline modifier is about 1 wt. % to about 15 wt. % of the total weight of the composition.

8. The composition of claim 1, further comprising an additive selected from the group consisting of 2-vinyl pyridine (V)/styrene (S) copolymer, ethyl cellulose, and mixtures thereof.

9. The composition of claim 1, further comprising one or more optional ingredients selected from the group consisting of diluents, fillers, bulking agents, pigments, opacifiers, other plasticizers, processing aids, and mixtures thereof.

10. The composition of claim 1, wherein said composition effectively masks the taste of the drug ingredient.

11. A medicament comprising:
    an effective amount of a drug ingredient having an unpleasant taste; and
    a coating composition for masking the taste of the drug ingredient and enhancing release of the drug ingredient in the stomach, the drug ingredient being coated by the coating composition, the coating composition comprising a taste masking blend of:
    (a) polyvinyl acetate;
    (b) dimethylaminoethyl methacrylate and neutral methacrylic acid ester; and
    (c) an alkaline modifier; the alkaline modifier being present in the coating composition, as a component thereof, in an amount sufficient to increase the coating composition's dissolution rate in the stomach, as compared to a like coating composition that does not contain the alkaline modifier, the unpleasant taste of the drug ingredient being masked when the medicament is orally ingested, the drug thereafter being rapidly and substantially completely released in the stomach.

12. The medicament of claim 11, wherein the drug ingredient is selected from the group consisting of particles, granules, powders, and mixtures thereof.

13. The medicament of claim 11, wherein said polyvinyl acetate polymer is about 3 wt. % to about 97 wt. % of the total weight of the composition.

14. The medicament of claim 11, wherein said dimethylaminoethyl methacrylate and neutral methacrylic acid ester is about 3 wt. % to about 97 wt. % of the total weight of the composition.

15. The medicament of claim 11, further comprising an additive selected from the group consisting of ethyl cellulose, polyvinylpyrrolidone, 2-vinyl pyridine (V)/styrene (S) copolymer, and mixtures thereof.

16. The medicament of claim 11, further comprising one or more optional ingredients selected from the group consisting of diluents, fillers, bulking agents, pigments, opacifiers, other plasticizers, processing aids, and mixtures thereof.

17. The medicament of claim 11, wherein said alkaline modifier is selected from the group consisting of triethanolamine, basic amino acids, talc, ammonium oleate, meglumine, trimethylamine, calcium silicate, aluminum magnesium silicate, food alkalizing agents, and mixtures thereof.

18. The medicament of claim 11, wherein said alkaline modifier is about 0.2 wt. % to about 20 wt. % of the total weight of the composition.

19. The medicament of claim 11, wherein said alkaline modifier is about 2 wt. % to about 4 wt. % triethanolamine, and about 4 wt. % to about 8 wt. % other alkaline modifiers.

20. The medicament of claim 11, wherein the drug ingredient is selected from the group consisting of acetaminophen, aspirin, ibuprofen, dexibuprofen lysinate, naproxen, ketoprofen, lactam, quinolone, macrolide and salts thereof, loperamide, famotidine, ranitidine, cimetidine and salts thereof, ibersartan, captopril, lisinopril and salts thereof, nefzodone, buspirone and salts thereof, chlorpheniramine, astemizole, pseudoephedrine, statins, antivirals, anticancer, antiplatelet, vitamins, minerals, psyllium, and mixtures thereof.

21. The medicament of claim 11, wherein said medicament is selected from the group consisting of: chewable tablets, powders for reconstituted suspensions, regular liquid form of prepared suspensions, fast dissolving quick melt tablets, lozenges, wafers, chewing gums, hard shell gelatin capsules with powder/granules/liquid fills, soft shell gelatin with liquid center or filled with powder or granules, regular compressed tablets with immediate or delayed release, candy and candy bar forms, aerosol creams, and gels.

22. The medicament of claim 11, wherein the medicament is a tablet formed by compressing coated granules.

23. The medicament of claim 11, wherein the medicament has a ratio of coating composition to drug ingredient that is about 1:50 to 3:1.

24. The medicament of claim 23, wherein said ratio is about 1:10 to 2:1.

25. A medicament comprising:
    an effective amount of a drug ingredient having an unpleasant taste; and
    a coating composition for masking the taste of the drug ingredient and enhancing the release of the drug ingredient in the stomach, the drug ingredient being coated by the coating composition, the coating composition comprising a taste masking amount of a blend of:
    (a) polyvinyl acetate in an amount of about 3 wt. % to about 97 wt. % of the total weight of the composition;
    (b) dimethylaminoethyl methacrylate and neutral methacrylic acid ester in an amount of about 3 wt. % to about 97 wt. % of the total weight of the composition;
    (c) an alkaline modifier in an amount of about 0.2 wt. % to about 20 wt. % of the total weight of the composition; and
    (d) an additive selected from the group consisting of polyvinylpyrrolidone, 2-vinyl pyridine (V)/styrene (S) copolymer, ethyl cellulose, and mixtures thereof; the amount of the alkaline modifier being sufficient to increase the coating's dissolution rate in the stomach, as compared to a like medicament in which the drug ingredient is coated with a like coating composition that does not contain the alkaline modifier, the unpleasant taste of the drug ingredient being masked when the medicament is orally ingested, the drug ingredient thereafter being rapidly and substantially completely released in the stomach.

26. The medicament of claim 25, wherein the medicament has a ratio of coating composition to drug ingredient that is about 1:50 to 3:1.

27. The medicament of claim 26, wherein said ratio is about 1:10 to 2:1.

28. A medicament comprising:

an effective amount of a drug ingredient; and a coating composition for masking the taste of the drug ingredient and enhancing the release of the drug ingredient in the stomach, the drug ingredient being coated by the coating composition, the coating composition comprising a taste masking blend of:
- (a) polyvinyl acetate in an amount of about 28 wt. % of the total weight of the composition;
- (b) dimethylaminoethyl methacrylate and neutral methacrylic acid ester in an amount of about 28 wt. % of the total weight of the composition;
- (c) ethyl cellulose in an amount of about 28 wt. % of the total weight of the composition;
- (d) talc in an amount of about 5 wt. % of the total weight of the composition;
- (e) other alkaline modifier in an amount of about 3 wt. % to about 11 wt. % of the total weight of the composition; the amount of the talc and other alkaline modifier being sufficient to increase the coating's dissolution rate in the stomach, as compared to a like medicament in which the drug ingredient is coated with a like coating composition except that it does not contain talc or said other alkaline modifier as a component thereof, the unpleasant taste of the drug ingredient being masked when the medicament is orally ingested, the drug ingredient thereafter being rapidly and substantially completely released in the stomach.

29. The composition of claim 9, wherein said processing aid is selected from the group consisting of sodium lauryl sulfate, colloidal silica, silicon dioxide and mixtures thereof.

30. The composition of claim 16, wherein said processing aid is selected from the group consisting of sodium lauryl sulfate, colloidal silica, silicon dioxide and mixtures thereof.

31. Method for increasing the release rate of an unpleasant tasting active in a chewable tablet containing same, the active being coated with a coating composition containing a taste masking blend of polyvinyl acetate and dimethylaminoethyl methacrylate and neutral methacrylic acid ester, comprising incorporating an alkaline modifier in the coating composition and adjusting the amount of the alkaline modifier that is incorporated so that the unpleasant taste of the active is masked when the tablet is chewed and the active is rapidly and substantially completely released in the stomach.

32. The composition of claim 1, wherein said dimethylaminoethyl methacrylate and neutral methacrylic acid ester is about 3 wt. % to about 28 wt. % of the total weight of the composition.

33. The composition of claim 1, wherein said dimethylaminoethyl methacrylate and neutral methacrylic acid ester is about 28 wt. % of the total weight of the composition.

34. The medicament of claim 11, wherein said dimethylaminoethyl methacrylate and neutral methacrylic acid ester is about 3 wt. % to about 28 wt. % of the total weight of the composition.

35. The medicament of claim 11, wherein said dimethylaminoethyl methacrylate and neutral methacrylic acid ester is about 28 wt. % of the total weight of the composition.

36. The medicament of claim 25, wherein said dimethylaminoethyl methacrylate and neutral methacrylic acid ester is about 3 wt. % to about 28 wt. % of the total weight of the composition.

37. The medicament of claim 25, wherein said dimethylaminoethyl methacrylate and neutral methacrylic acid ester is about 28 wt. % of the total weight of the composition.

38. The composition of claim 1, wherein the drug ingredient or medicine is completely released in the stomach.

39. The medicament of claim 11, wherein the drug ingredient is completely released in the stomach.

40. The medicament of claim 25, wherein the drug ingredient is completely released in the stomach.

41. The medicament of claim 28, wherein the drug ingredient is completely released in the stomach.

42. The method of claim 31, wherein the active is completely released in the stomach.

* * * * *